(12) United States Patent
Evans (10) Patent No.: US 9,063,065 B2
(45) Date of Patent: Jun. 23, 2015

(54) SAMPLE ANALYSIS (75) Inventor: Paul Evans, Nottingham (GB)

(73) Assignee: The Nottingham Trent University, Nottingham (GB)

( * ) Notice: Subject to any disclaimer, the term of this patent is extended or adjusted under 35 U.S.C. 154(b) by 169 days.

(21) Appl. No.: 13/703,679

(22) PCT Filed: Jun. 20, 2011

(86) PCT No.: PCT/GB2011/051151
§ 371 (c)(1),
(2), (4) Date: Feb. 1, 2013

(87) PCT Pub. No.: WO2011/158047
PCT Pub. Date: Dec. 22, 2011

(65) Prior Publication Data
US 2013/0208859 A1    Aug. 15, 2013

(30) Foreign Application Priority Data
Jun. 18, 2010    (GB) .................................. 1010233.3

(51) Int. Cl.
*G01N 23/201*    (2006.01)
*G01N 23/083*    (2006.01)
*G06K 9/46*    (2006.01)
*G06K 9/60*    (2006.01)
*G01N 23/20*    (2006.01)
*G06T 7/00*    (2006.01)
*G01V 5/00*    (2006.01)

(52) U.S. Cl.
CPC ........ *G01N 23/20083* (2013.01); *G01N 23/083* (2013.01); *G01V 5/0033* (2013.01); *G01N 23/201* (2013.01); *G06T 7/0002* (2013.01); *G06T 2207/10116* (2013.01)

(58) Field of Classification Search
CPC ................... G06T 7/0002; G06T 2207/10116; G01N 23/083; G01N 23/201; G01N 23/20083; G01V 5/0033
USPC .............. 378/51, 53–57, 70, 86–88, 90, 98.8, 378/147, 204, 210
See application file for complete search history.

(56) References Cited

U.S. PATENT DOCUMENTS

| 5,583,904 A | 12/1996 | Adams |
| 6,324,249 B1 | 11/2001 | Fazzio |

(Continued)

FOREIGN PATENT DOCUMENTS

| EP | 2 151 681 A1 | 2/2010 | |
| WO | WO-2008/149078 A1 | 12/2008 | |
| WO | WO 2008149078 A1 * | 12/2008 | ............. G01N 23/20 |

OTHER PUBLICATIONS

Steinmetz, Johannes, "International Search Report" for PCT/GB2011/051151, as mailed Sep. 9, 2011, 4 pages.

(Continued)

*Primary Examiner* — Anastasia Midkiff
(74) *Attorney, Agent, or Firm* — Winstead PC (57) ABSTRACT

A method of sample analysis comprises irradiating a sample with electromagnetic radiation such as X-rays; collecting absorption data and scattering data; and combining the absorption and scattering data. The irradiation can be in the form of a tubular beam, a detector may be placed in a plane where Debye cones diffracted from the sample overlap at a central point for the collection of the scattering data.

16 Claims, 8 Drawing Sheets (56) References Cited

U.S. PATENT DOCUMENTS

2005/0008120 A1* 1/2005 Ellenbogen .................... 378/57
2010/0111255 A1   5/2010 Harding

OTHER PUBLICATIONS

Rogers, Keith, et al., "Focal construct geometry—a novel approach to the acquisition of diffraction data", Journal of Applied Crystallography, vol. 43, No. 2, Mar. 11, 2010, pp. 264-268.

* cited by examiner

SAMPLE ANALYSIS

TECHNICAL FIELD

The present invention relates to Improvements in sample analysis, and in particular the analysis of samples by irradiating the sample with electromagnetic radiation.

BACKGROUND

The invention can relate to any type of electromagnetic radiation but has particular utility for X-rays. Electromagnetic waves having wavelengths in the range of 0.01 to 10 nm are known as X-rays. X-rays have energies in the range of 120 eV to 120 keV.

It is known to image objects using X-rays by measuring X-ray absorption. Typically this involves having an X-ray source and detector with a sample in between them. The primary X-ray beam is directed towards and hits the sample, with some of the X-ray radiation being absorbed, a smaller amount being scattered and the remainder going on to hit the detector.

X-ray absorption imaging is reasonably effective for imaging the shape of a structure, however reliance on the absorption characteristics of the objects under inspection produces low overall accuracy in terms of material identification. For example dual-energy X-ray imaging exploits the difference in atomic cross section between the photoelectric absorption and the Compton scattering processes inferred by the relative change in magnitude of a high-energy X-ray signal and a low-energy X-ray signal. Consequently an appropriately calibrated X-ray system may be employed to broadly discriminate an inspected object into a limited number of material classes. The discrimination information may be presented to the human observer by colour coding the resultant X-ray images. Thus, for example, security personnel in an airport might review the contents of bags going through an X-ray scanner and can look at the pseudo colours displayed as well as the shape to identify anything suspicious.

Such X-ray absorption techniques can be used in real time and on every day objects, however such techniques allow only for crude discrimination of materials. Existing absorption techniques are not adequate for distinguishing between materials that have similar chemical signatures, or for detection of objects that have flat shapes. For example, X-ray absorption imaging is unsuitable for the identification of precise material useful to find explosive substances or contraband drugs.

It is also known to solve the structure of a crystal by analysing the scattering of X-rays through a crystal, for example by analysing the diffraction pattern produced. This is known as X-ray crystallography.

A small portion of a primary X-ray beam incident onto a crystal is scattered at measurable angles if its wavelength is similar to the lattice distances (or d-spacing) present in the crystalline material under inspection. For ideal, polycrystalline materials interrogated by pencil beams, the photon scatter follows a cone distribution, with the source of the scattering at the cone apex. These "Debye cones" form circular patterns when they intersect a flat detector normally. These circles have a common centre coincident with that of the incident beam position on the detector. The angular distribution of the scattered intensity is unique to each different crystal structure and thus can be used to identify a material and determine characteristics such as lattice dimensions, crystallite size and percentage crystallinity. The key relationship between the lattice spacing (d), and the scatter angle ($\theta$) is embodied within the well known Bragg condition: $\lambda=2d \sin \theta$ (where $\lambda$ is the X-ray wavelength).

X-ray crystallography allows for the structure of a large number of molecules of different materials including inorganic compounds to be determined. Ordinarily this is done with single crystals though it is possible to obtain significant information from powdered material or from thin films. This technique allows a large amount of information about materials to be determined. However, even where powders rather than single crystals are used it is a requirement to prepare a custom made small sample which is then bombarded with X-rays perhaps over many hours to provide adequate detection and subsequent analysis of the diffraction pattern.

Conventional powder diffractometers utilise detectors to scan and measure a portion of the resultant diffraction pattern. This angular dispersive technique usually employs monochromatic X-rays. Data collection and analysis have been based mainly on one-dimensional (1D) intensity profiles obtained with scanning point detectors or linear detectors. The linear detector is often referred to in the field as a position sensitive detector or PSD. The use of 2D image sensors (array or area detectors) may be used to speed up the collection of data in comparison to point or line detectors. However the collection process is still relatively slow.

Some of the commonly used X-ray scattering techniques are: single crystal diffraction (SCD), X-ray powder diffraction (XRPD), high-resolution X-ray diffraction (HRXRD), X-ray reflectometry (XRR) and small angle X-ray scattering (SAXS). In general diffractometers are laboratory instruments which are designed for off-line inspection requiring relatively long periods of data collection from carefully prepared samples, because the amount of radiation that is scattered is relatively low and therefore long integration periods are required in order to accumulate a sufficient amount of signal for accurate measurement. For this and other reasons X-ray crystallography can be a very effective technique in laboratories for slow analysis but would not generally be suitable for every day objects or for use in "real time" or "on-line" inspection applications.

Bragg diffraction may occur whenever the wavelength of incident radiation is of a similar magnitude to the lattice spacing of a crystal under analysis, and so crystallography techniques are not limited to X-rays. Particles such as neutrons or electrons can be used if at the correct energy; as well as other electromagnetic radiation.

Figure 2:
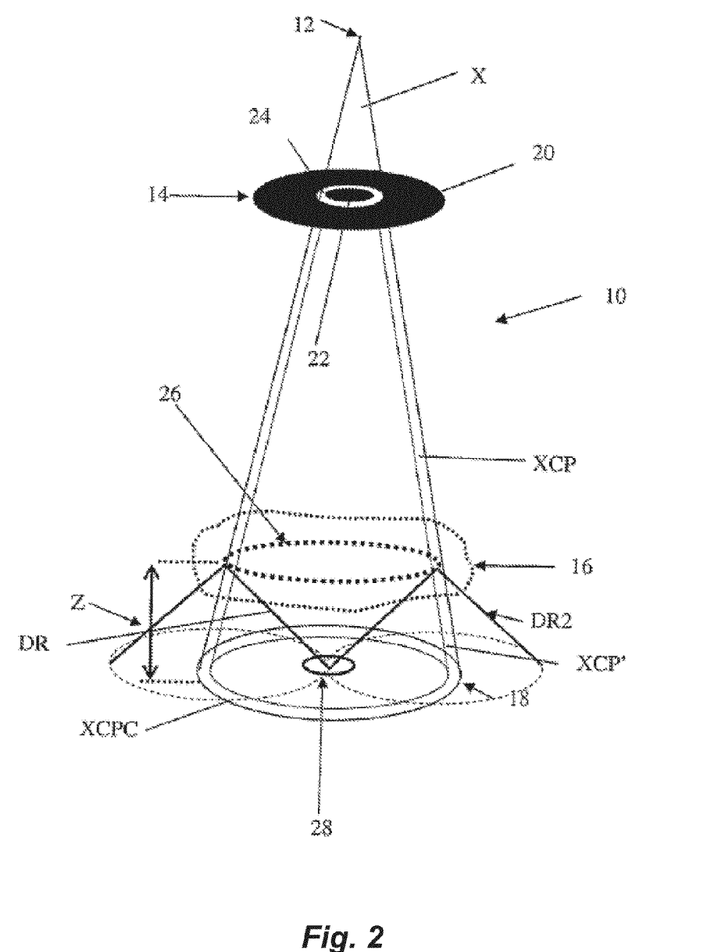
FIG. 2 is a schematic view of a prior art X-ray scatter gathering apparatus.
Figure 3:
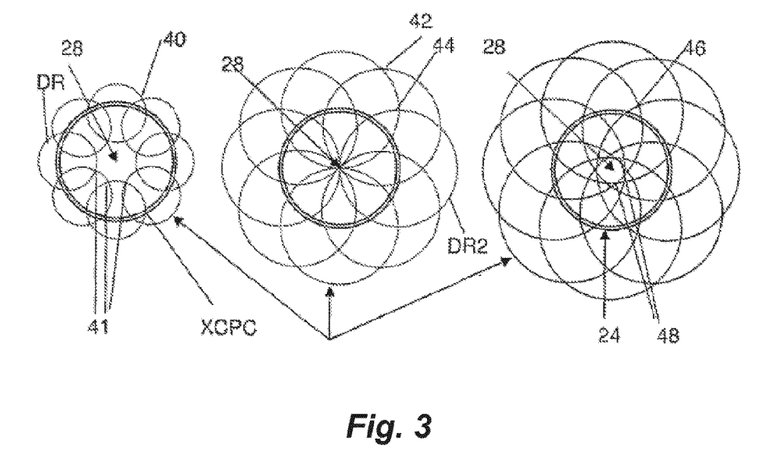
FIG. 3 is a view of the footprints of Debye cones generated at the receiving surface of the apparatus of FIG. 2.
Figure 4:
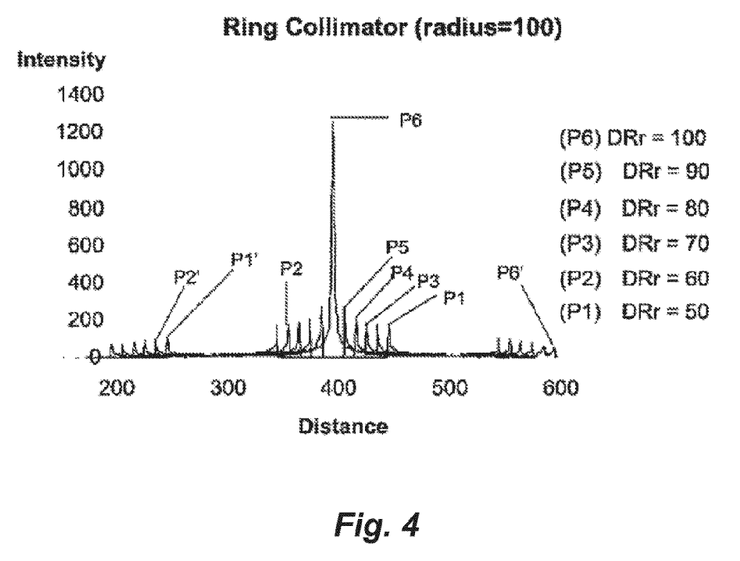
FIG. 4 is a chart of the intensity of X-rays received at the receiving surface in FIG. 2 and FIG. 3 depicted against the distance from a given point on the receiving surface.

An alternative technique is disclosed in WO 2008/149078, which is incorporated herein by reference, as well as being illustrated in FIGS. 2-4. The output of an X-ray source is configured, for example by an annular collimator, to form a curtain of X-ray radiation, which can be tubular and/or cone shaped for example. A detector is placed at a position where the Debye cones of X-ray radiation emitted from a sample overlap to form regions of increased intensity, which leads to increased sensitivity and better material discrimination. The technique can be performed over a much shorter time period than that of standard X-ray crystallography.

However, improvements in imaging and/or material detection are still highly sought after.

SUMMARY

According to a first aspect of the present disclosure, there is provided a method of sample analysis comprising: irradiating a sample with electromagnetic radiation; collecting electromagnetic radiation absorption data; collecting electromagnetic radiation scattering data; and combining said absorption and scattering data.

"electromagnetic radiation scattering data" refers to radiation that is scattered or diffracted, either coherent or incoherent. "electromagnetic radiation absorption data" refers to data gathered from the absorption or transmission of electromagnetic radiation through an object.

Optionally, the irradiating electromagnetic radiation comprises at least one tubular beam. The shape of the tubular beam can be right circular cylinder or a cone. The sidewalls of the tubular beam may have a definite or a predetermined width. Optionally, the tubular beam is formed by passing the electromagnetic radiation rays through a collimator that comprises an electromagnetic radiation blocking body portion and one or more electromagnetic radiation transmitting apertures, the shape of which defines the shape of the tubular beam or beams.

Optionally, the collection of electromagnetic radiation absorption data comprises a laminographic technique.

Optionally, the collection of electromagnetic radiation scattering data comprises placing a detector in a plane where Debye cones diffracted from the sample overlap at a central point.

Optionally, the method comprises obtaining position information from the absorption data, matching a feature in the absorption data with a feature in the scattering data; and corresponding the position information from the absorption data to the scattering data.

Optionally, the method comprises irradiating electromagnetic radiation in a first conical beam having a first opening angle, and a second conical beam having a second opening angle. Optionally, both conical beams share a common point source. The relative opening angles of the first and second conical beams can be chosen such that both beams are directed towards different detectors or different portions of a detector so that the interference of signals detected by one detector or one detector portion and signals detected by the other detector or other detector portion is reduced or minimised.

Optionally, a sequence of images is displayed to a user. The sequence can be animated.

Optionally, the electromagnetic radiation comprises X-rays.

According to second aspect of the disclosure there is provided a method of material identification and/or discrimination comprising: irradiating a sample with electromagnetic radiation; collecting electromagnetic radiation absorption data; collecting electromagnetic radiation scattering data; combining said absorption and scattering data; and matching the combined data with known material characteristics.

The method of the second aspect may make use of any of the steps of the first aspect.

According to a third aspect of the disclosure there is provided a sample analysis apparatus, comprising an electromagnetic radiation source; a detector for collecting electromagnetic radiation absorption data; a detector for collecting electromagnetic radiation scattering data; and a processor for combining said absorption and scattering data.

Optionally, the detector for collecting electromagnetic radiation absorption data and the detector for collecting electromagnetic radiation scattering data are provided as different portions of a master detector Optionally, the detector for collecting electromagnetic radiation absorption data comprises a ring sensor.

Optionally, the detector for collecting electromagnetic radiation scattering data is provided within the bounds of the ring sensor.

The apparatus may comprise means for carrying out any of the steps of the first two aspects.

According to a fourth aspect of the disclosure there is provided a computer program product, that when run on a computer, enables that computer to perform functions required for the methods of the first two aspects, and forms part of the apparatus of the third aspect.

The computer program product can be downloaded or downloadable onto, or provided with, a computing device such as a desktop computer, in which case the computer that comprises the computer program product provides further aspects of the invention.

The computer program product may comprise computer readable code embodied on a computer readable recording medium. The computer readable recording medium may be any device storing or suitable for storing data in a form that can be read by a computer system, such as for example read-only memory (ROM), random-access memory (RAM), CD-ROMs, magnetic tapes, floppy disks, optical data storage devices, and carrier waves (such as data transmission through packet switched networks such as the Internet, or other networks). The computer readable recording medium can also be distributed over network coupled computer systems so that the computer readable code is stored and executed in a distributed fashion. Also, the development of functional programs, codes, and code segments for accomplishing the present invention will be apparent to those skilled in the art to which the present disclosure pertains.

BRIEF SUMMARY OF FIGURES

The present invention will be described, by way of example only, with reference to the accompanying drawings, in which.

DETAILED DESCRIPTION

Figure 1:
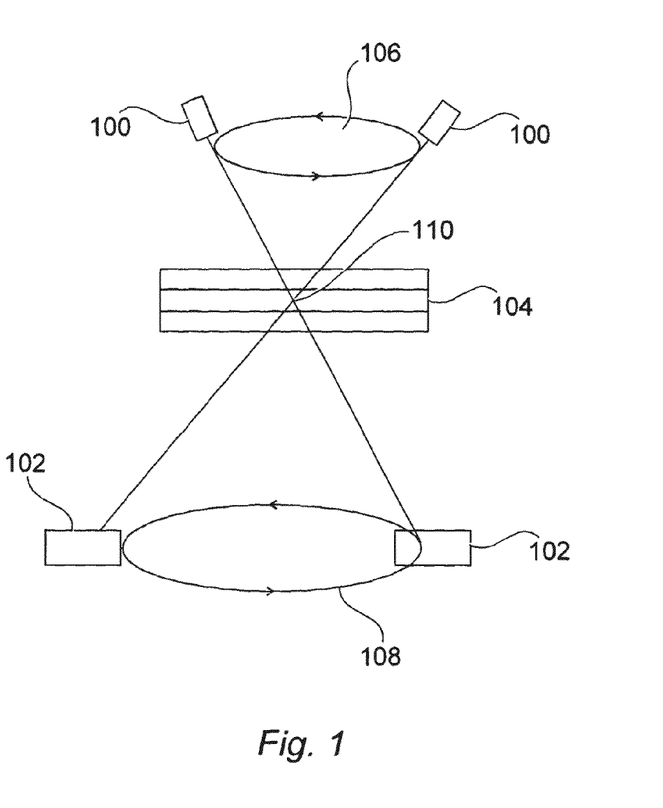
FIG. 1 shows the principles of laminography.

Laminography is a technique used to image specific layers of an object. Aspects of a laminography apparatus are illustrated in FIG. 1. The apparatus comprises a radiation source 100 and a radiation detector 102. Both the radiation source 100 and detector are shown for the purposes of illustration in two different illustrative positions. An object 104 is placed between the source 100 and the detector 102. Laminography, relies upon coordinated motion of any two of the source 100, detector 102 and object 104. In the illustrated apparatus, motion of the source 100 and the detector is coordinated. They move in the paths 106, 108 indicated which in this example are synchronous circular paths in the same sense about a common rotational axis. The coordinated motion of the two components can be in a variety of patterns other than circular, such as linear, elliptical or random patterns.

An image plane is formed at the intersection 110 of the chief ray from the source 100 and the axis of rotation of the source 100. The configuration of the source 100, detector 102 and object 104 is such that any point in the object plane is always projected to the same point in the image plane, while points outside the image plane are projected to different points in the image plane at different positions of the sensor/detector along its path of motion, (effectively a parallax effect), thus creating a blurred background, in contrast to the sharp image at object plane containing the intersection 110, that is, a cross-sectional image of the object 104 in that plane is produced.

When first proposed, the detectors comprised photographic film, which was developed over the period of the motion of the components of the apparatus. However it is now possible to use a digital image sensor, such as a CCD sensor, for example; or an array of such sensors, to detect the image data. Images at each successive position of the source/detector along the paths of motion can be stored to enable comprehensive data analysis and image reconstruction. The cross-sectional images derived are known as laminograms.

Tomography is a well known technique for creating an image of sections of an object. Relative motion of a radiation source and a detector causes structures in the focal plane of the set-up to appear sharply in focus while images from outside the focal plane become blurred. Thus, in contrast to projection imaging, where features at different depths overlap each other in the resultant image, features at the focal plane can be "picked out" from the rest of the object. Different focal planes can be selected by modifying the direction and extent of the movement, or by moving the object.

Computational, or computed, tomography involves the generation of a three-dimensional image of an object through the combination of a series of images taken over 360 degrees about an axis of rotation. Many different reconstruction algorithms exist, including filtered back projection and iterative reconstruction algorithms. This technique is used in X-ray computational tomography devices, commonly known as "CAT" or "CT" scanners".

Direct tomography involves the collection of scattering data in a scenario where the origin of the object is already known from the geometrical arrangement of the apparatus. The imaging geometry is set up so that the location of volume elements, known as voxels, is known, and the radiation is viewed through a collimator that shapes the radiation into known patterns or arrangements. This means that synthesis of the collected scattering data including the performance of an inverse Radon transformation is not required because the knowledge of where in object space the data comes from is already known from the positions of the radiation sources and the detectors. The imaging geometry is set up so that the location of volume elements, known as voxels, is known. The set up of FIGS. 2-4 is an example of a "direct tomography" system.

Tomosynthesis is a technique that combines digital image capture and processing with relative motion of a radiation source and radiation detector. However, in contrast to standard computational tomography, a relatively small angle of rotation is used, say forty degrees or so. This data set can be digitally processed to produce images, but with a limited depth of field. However, a series of cross-sectional images at different depths and with different thicknesses can be reconstructed from the same acquisition, saving both time and radiation exposure of the object being scanned. Because the data acquired is incomplete, tomosynthesis is unable to offer the extremely narrow slice widths that computational tomography offers. However, higher resolution detectors can be used, allowing very-high in-plane resolution, even if the Z-axis resolution is poor. Tomosynthesis is therefore useful in breast imaging, where it may offer better detection rates with little extra increase in radiation exposure.

A tubular beam is defined in this disclosure as a beam that has a shape of a hollow cylinder, where a cylinder is defined in its general sense as a ruled surface spanned by a one-parameter family of parallel lines. As such, beams having the shape of hollow circular or elliptical cylinders or hollow cones are examples of tubular beams.

FIG. 2 shows an example of a prior art X-ray scatter gathering apparatus 10. The apparatus 10 is suitable for carrying out X-ray crystallography, that is, to gather scattering data. The apparatus 10 comprises an X-ray source 12, a ring collimator 14, a target object 16, and a detection surface 18 which includes a detector or sensor.

Ring collimator 14 is made from a conventional material that might typically be used for collimating X-rays, such as tungsten or steel. Any material can be used so long as it can significantly block the path of X-rays. The ring collimator 14 comprises an annular aperture 24 between disc 22 and annulus 20. All three of the annulus 20, annular radius 24 and disc 22 have the same centre point. The disc 22 may be held in its position relative to the annulus 20 by any appropriate means such as being attached via thin wire or by being held in place using electromagnets. Annulus 20 does not need to be circular, rather it needs simply to block the primary beam. A target object 16 is the target from which the apparatus 10 is designed to detect diffracted X-rays. It may comprise a material suspected to be a polycrystalline material and which it is wished to identify. The target object can be of numerous forms but in the example depicted in FIG. 2 it is a plate like object which has a width larger in diameter than the curtain XCP of X-ray radiation that passes through the aperture but that does not have a substantial depth.

The detection surface 18 may comprise a physical surface or it can be the name given to a plane of a hypothetical surface with no physical surface present. Somewhere on the surface 18 (or alternatively along the plane) is a sensor, which can be located at the centre of surface 18 directly in line with the X-ray source and the centre of the ring collimator 14.

In use the X-ray source produces a cone of X-rays (X) which is aimed towards and therefore incident on the ring collimator 14. The disc 22 and annulus 20 are made of attenuating material so that they block the majority of these X-rays (X). However, X-rays do go through the annular aperture 24 and this results in the production of a conical curtain of X-rays XCP. The cross section of the conical curtain XCP will be a narrow annulus of X-rays, that is the X-rays are present in the shape of a band between a first cone and a second cone which can be imagined to be positioned at a point slightly higher than the first cone. A further possibility, depending on the size of the source 12, is that the cones share the same primary axis and apex position but have different opening angles.

The conical curtain XCP hits the target object 16. Since the target object is substantially planar the conical curtain XCP hits the object 16 in a circular target path 26. Some of these X-rays will be scattered by the lattice of the target object 16 by Bragg diffraction and some absorbed, but much of the primary X-ray radiation will continue. There is a substantially continuous X-ray curtain XCP' which then hits the detection surface 18 a distance Z from the target object 16, forming an annulus of primary X-rays XCPC at that surface 18. In the embodiment described the sensor is present at the centre of the surface and has a radius sufficiently small that it is contained within the inner radius of annulus XCPC and therefore none of the primary X-ray beam is detected.

Because the target object 16 contains a polycrystalline material with a certain d-spacing there is X-ray diffraction causing a scatter of the photons in a conical distribution. As mentioned above these are known as "Debye cones" and they are generated from every point along the circular target path 26 so long as the crystal structure is present. Two such Debye cones are marked in FIG. 2 as DR and DR2. It has been found that a "hotspot" 28 can be generated in the centre of the detection surface 18 provided the distance Z is set correctly and for this reason the detector is preferably designed to be coincident with hotspot 28.

FIG. 3 shows a superposition of the cross-sections, or "footprints" of some Debye cones from the target object 16 at the detection surface 18 with different distances Z shown in the left, middle and right diagrams. In all three examples the annulus of primary X-rays XCPC is illustrated for comparison purposes.

In the left-side diagram of FIG. 3, the detection surface 18 is at a distance Z where the diameters of the Debye cones are still significantly smaller than the diameter of the circular target path 26. As can be seen there is a series of circles produced by Debye cones including circles corresponding to DR and DR2. At certain points 40 the circles overlap thus increasing the intensity at those points to approximately double elsewhere on the circle. However there are no circular paths through the centre, which results in an approximately zero intensity of X-rays in the hotspot 28. The hotspot is the centre, where the sensor is present.

In the middle diagram of FIG. 3, the detection surface 18 is at a distance Z where the diameters of the Debye cones are equal to the diameter of the circular target path 26. There are numerous overlapping points such as point 42 and point 44 where two or three cones coincide increasing the intensity of X-ray radiation at those points. Most significantly however, all of the cones contribute to the intensity at the very centre of detection surface 18 at hotspot 28 where the sensor is present. Accordingly the intensity of radiation at this point is greatly increased.

In the right-side diagram of FIG. 3 the detection surface 18 is at a greater distance Z where the diameters of the Debye cones are now significantly larger than the diameter of the circular target path 26. In this example there are several points of overlap between the circles of the Debye cones such as points 46 and 48. However there is no point where all of the cones are coincident. Significantly none of the circles pass through the centre/hotspot 28 and therefore there is approximately zero intensity of X-rays in the centre where the sensor is present.

Accordingly there is substantially zero X-ray radiation detected at the sensor at the hotspot 28 in the right-side and left-side diagrams of FIG. 3 whilst there is a great intensity from each of the cones concentrating on a single point in the central hotspot in the middle diagram of FIG. 3. For this reason, for a particular polycrystalline material that needs to be identified, the d-spacing and therefore the scattering angle can be calculated so that for a given ring collimator 14 and distance between collimator and sample, the correct distance Z can be calculated where the situation of the middle diagram of FIG. 3 should exist, that is, where the Debye cones will have the same diameter as the target path 26 in the plane 18 of the sensor. The distance can be fine tuned in practice by moving any of the target object 16, collimator 14 or detection surface 18 so that the maximum radiation intensity is found.

Because the massive difference in intensity at the centre between the diagrams of FIG. 3 depends on the distance Z, the apparatus 10 can be used for an unspecified polycrystalline material. The target object 16, collimator 14 or detection surface 18 can be linearly moved whilst still in line with each other until the detector picks up the large reading of intensity at the centre associated with the situation in the middle diagram of FIG. 3. The distances between two or more of the ring collimator 14, detection surface 18 and target object 16 can be measured allowing the angle of scatter of the Debye cones and therefore the d-spacing to be calculated. The material can then be identified on the basis of the calculated d-spacing, as the association of particular d-spacings with particular materials is well established.

In FIG. 2 for ease of illustration the footprint of the Debye cones are shown, as circular. This situation implies the Debye cones emanate from a fixed height from the detector and result from a cylindrical curtain of primary X-rays. In fact the cross section of Debye cones including cones DR and DR2 in FIG. 1 when intersected by a plane normal to the right conical curtain of primary X-rays will produce elliptical patterns. However, this observation will not change the working principle of the invention and is believed to be easier to illustrate with circles rather than ellipses.

It can also be seen that in the left-side diagram of FIG. 3 there is a circular configuration of intersection points 41. Since there are a very large number of evenly spaced Debye cones the intersection points for all cones produce a circular configuration of increased intensity which will form a closing ring around the hotspot 28. In the right-side diagram of FIG. 3 there is a similar closing ring of intersection points 48. These closing rings represent a region of increased intensity but, one that still has significantly less intensity than the centre 28 in the middle diagram of FIG. 3.

FIG. 4 shows the intensity (in arbitrary units) in the central region of the detector surface 18 for different radii of circular cross sections of Debye cones (similar results would be present for elliptical cross-sections), for a circular target path 26 that has a radius of 100 arbitrary units. Peak P1 represents the intensity of X-ray radiation found at the detection surface 18 from the closing ring from a Debye ring radius of 50 AU. Peak P1' represents the intensity of X-ray radiation found at the detection surface 18 from a further ring from a Debye ring radius of 50 AU formed by the closing ring. The intensity at both P1 and P1' is low, being slightly higher at P1' as this point is closer to the centre where the radius is smaller and therefore concentration of intersections of cones is greater. Peaks P2 and P2' represent intensity rings from a Debye cone radius of 60 AU. As well as being more spaced there is a slightly higher intensity in the peaks. As the Debye radius increases to 70, 80 and 90 AU as seen from the respective peaks illustrated by P3, P4 and P5, each time the peaks get slightly further away and have very slightly increased intensities. However when the Debye ring radius is 100 AU, then P6 and P6' are generated. Whilst P6' (which is now 200 AU away from the centre) isn't of great intensity, P6, which is coincident with a hotspot 28, has a much greater intensity level than all of the other peaks. Accordingly, at this point far more radiation can be measured and the sensor need only be small if positioned at the hotspot 28.

The apparatus and methods of the present disclosure provide for the collection of both X-ray absorption data and X-ray scattering data.

An apparatus according to a first embodiment may enable a novel imaging technique, reliant upon critical component design that collects simultaneously high intensity coherent X-ray scatter signals and X-ray absorption data. The approach can utilise a configuration of a tubular X-ray beam incident upon a ring 'absorption' sensor and a central 'scattering or diffraction' sensor. The relative translation (or rotation) of the object under inspection enables image scanning in 2D and 3D. The following text discusses the X-ray scattering and absorption components of the technique independently.

For the collection of the X-ray scattering data, a continuum of Debye cone elements from around a circular path converges to form a series of foci. A deconvolution of the data with an appropriate aperture restores the geometric properties of the resultant image. Orders of magnitude increase in the intensity of the diffraction signal is possible in comparison with conventional angular dispersive methods. Planar sections of object space may be interrogated with such an approach.

A ring sensor collects absorption data from a circular path about each diffraction focus. The discreetly sampled ring sub-images may be reorganised to form a convergent multiple view sequence. Each feature point in the resultant image sequence exhibits radial parallax and appears to move along a circular path. This property enables, with appropriate synthesis, laminograms (i.e. images of planar sections through the object under inspection) to be produced.

FIGS. 5 to 9 illustrate the collection of X-ray absorption data. A tubular cone 600 of X-rays is provided by radiation source 602, via a collimator or other mechanism as described above.

Figure 5:
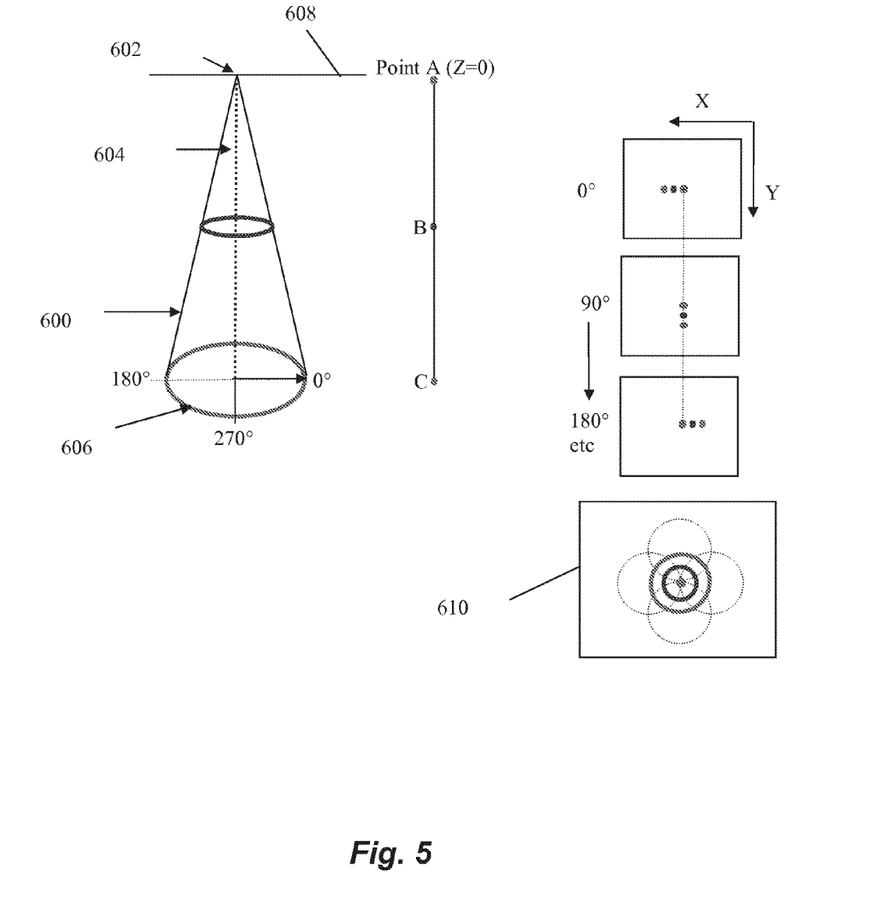
FIG. 5 shows the operation of a method of collecting absorption data according to a first embodiment.

The tubular cone 600 is symmetric about symmetry axis 604, which is referred to as the z-axis. A sensor is provided at a position 606. The z-axis 604 is normal to the plane of the sensor. The tubular cone 600 is incident on the sensor and forms a pattern with different angular positions, three of which are labelled as 0, 180 and 270 degrees. The angular position that is labelled as zero degrees can be chosen arbitrarily.

The principle of operation can be understood from considering the radiation at points A, B and C along the axis 604 (the points are illustrated beside the ray diagram for clarity, and the ray diagram shows the circular patterns formed by the tubular cone 600 in planes at each point). In FIG. 5, a focal plane 608 is formed at point A. Relative motion of the object with respect to the source 602 and detector (represented by plane 606) is achieved, either by moving the object or by synchronised motion of the source 602 and detector. After this x and y scanning, each cone element will produce a full image. The number of elements will be a matter of design choice. There may be a small number of elements, such as two or four, or a large number of elements, such as several thousand or several million, however for the purposes of illustration it is convenient to consider the case of one element at each degree of the circle produced by the cone in a plane.

At different angular positions, the points B and C will be imaged at different locations in the plane of the detector. Point A will always be imaged in the same location because it lies in the focal plane. In this example, point A is at the centre of the image. FIG. 5 comprises diagrams showing the points as they are imaged at 0, 90 and 180 degree field positions. The top diagram (zero degrees) shows points CBA left-to-right, the middle diagram (90 degrees) shows points ABC top-to-bottom and the lower diagram (180 degrees) shows points ABC left-to-right.

The composite image 610 for the case of a focal plane at z=0. All points A, B, C share the same x and y coordinates in object space, but in the composite image 610, because points B and C are outside the focal plane, the points are spread out and become dark rings (point B forms the inner dark ring and point C forms the outer dark ring, while point A remains in focus). Other points at different angular positions will also be blurred. In effect, a laminogram of the focal plane is formed.

Figure 6:
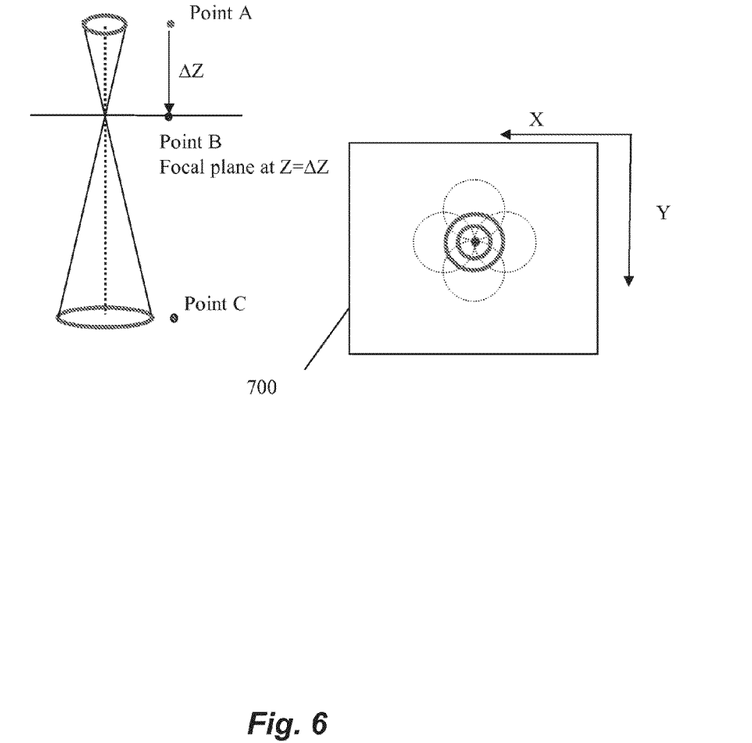
FIGS. 6-9 show further aspects of the operation of a method of collecting absorption data according to a first embodiment.

FIG. 6 shows a similar scenario for the case where the focal plane is formed at point B, at position Z=ΔZ. Again, the points A, B, C share common x and y positions. This time however, point B remains in focus and points A and C are spread out and become dark rings. In the composite image 700, point B is in focus at the centre, point A forms the inner dark ring and point C forms the outer dark ring.

Figure 7:
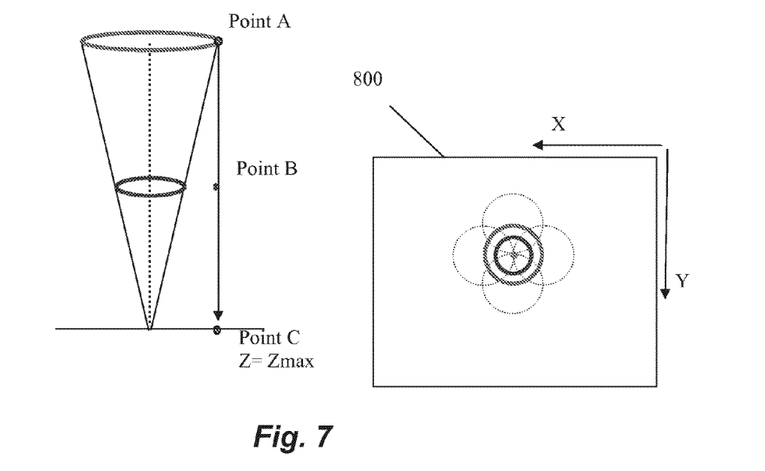

FIG. 7 shows a similar scenario for the case where the focal plane is formed at point C, at position Z=Zmax. Again, the points A, B, C share common x and y positions. This time however, point C remains in focus and points B and C are spread out and become dark rings. In the composite image 800, point C is in focus at the centre, point B forms the inner dark ring and point A forms the outer dark ring.

Figure 8:
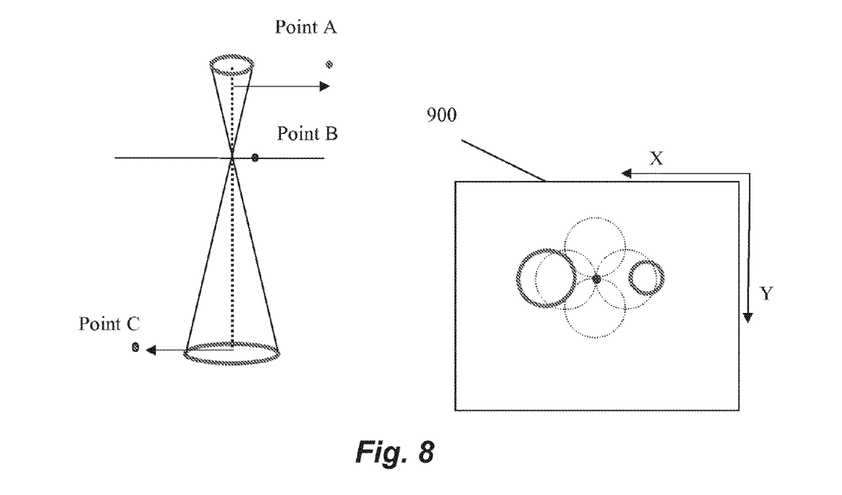

FIG. 8 shows a scenario where points A and C are displaced in an X-direction, but all points A, B and C share a common Y-position; and where the focal plane is formed at point B, at position Z=ΔZ. In the composite image 900, point B remains in sharp focus and at the centre of the image, while the blurred rings produced by points A and C are offset in the X-direction, point A forming the smaller dark ring on the right-side of the image and point C forming the larger dark ring on the left-side of the image.

Figure 9:
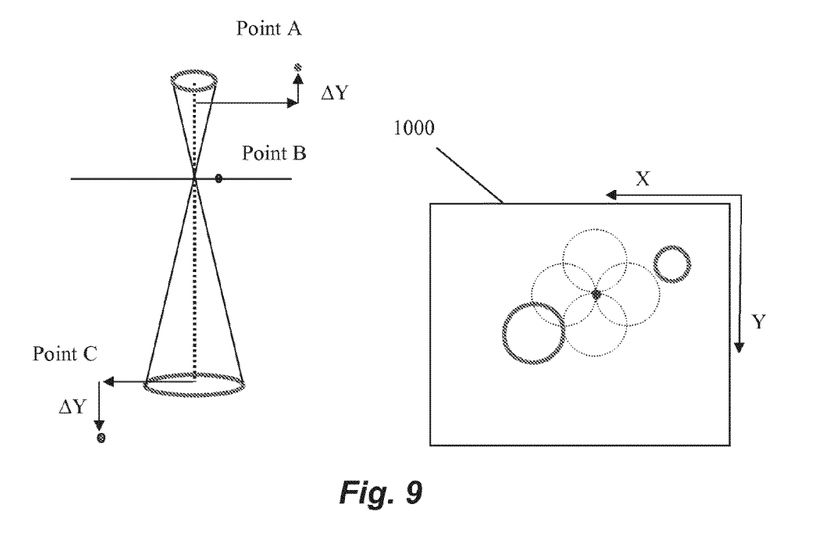

FIG. 9 shows a scenario where points A, B and C are all at different x,y positions; and where the focal plane is formed at point B, at position Z=ΔZ. In the composite image 1000, point B remains in sharp focus and at the centre of the image, while the blurred rings produced by points A and C are offset in the X and Y directions, point A forming the smaller dark ring on the upper-right-portion of the image and point C forming the larger dark ring on the lower-left-side of the image.

To produce the composite images shown in FIGS. 5-9, a raster scan in the x and y directions is carried out. The appropriate manipulation (geometric reconvergence along radial axes) of the resultant cone element images (produced by divergent x-rays from a point source) enables 'convergent' or focal plane views to be produced.

Each cone element is obtained from a different (x,y) sample position (with respect to the position of the symmetry axis).

The various circles represent the trajectory of the points as images at successive angular positions are inspected. That is, if the images were played as a movie, the points outside of the focal plane would move in a circular fashion and form the closed circles seen in the composite images.

Alternatively, if the image stack is appropriately aligned and summed i.e. applying digital tomosynthesis (to produce laminograms or cross section images/depth planes) then the circles indicate the geometry of the blurring produced by points not at the focal plane. The image data can be reconverged to focus on planes normal to the symmetry axis or Z-axis.

For each 'ring' sample acquired, a set of high intensity diffraction data can also be acquired from another detector. The common interrogating beam geometry enables the absorption data and the diffraction data to be mapped and interrelated.

Matching the spatial distribution of diffraction data to an absorption plane can be used to inform the analysis of the diffraction angles etc.

The mapping (or blending) of the diffraction images to the corresponding laminograms or perspective views, by virtue of a common X-ray beam geometry, provides the basis for a new 3D imaging modality. A particular advantage of this technique is that the diffraction image is mapped to a much higher resolution absorption image to provide increased 2D and 3D spatial information.

Knowledge of opening angles for interrogating cone diffraction, for an opening angle θ is a function of wavelength.

High penetrating x-rays, cone angle is smaller, but that goes against you for the laminography aspects, where a large opening angle gives greater depth resolution.

For direct tomography, the position of a feature of interest in an absorption image is known from the set-up of the apparatus. When a diffraction signal having the same shape as that feature is identified, the known coordinates from the absorption data can be matched to the scattering data, meaning that one can identify the scattering angle. When a sheet or planar sample is at a known position in a tubular beam, we collect the set of scattering data for different foci. The angles associated with the foci are known because of the fixed geometry. The position of the sample is still unknown, but the scattering sensor can receive signals over a large solid angle. Without collimation, the source position and beam angle are not known. However, the absorption data gives the location of a feature in space. The scattering data arises from a point in space, so the two can be matched to get a material signature.

An alternative matching technique can be based on the arrangement shown in FIGS. 2-4. The scattering sensor can be provided with a collimator, which enables preferential scanning of signals from particular planes.

Cones can be concentric—in one example, an outside cone can be used for the absorption data and an inner cone can be used for the scattering data.

The cones can have different opening angles.

In the inner cone, for scattering data, a narrow cone is required in order to achieve the convergence of the Debye cones.

In the outer cone, for absorption data, the diffracted Debye cones will not converge, or will diverge. A large opening angle will be advantageous to achieve a larger depth resolution.

Sizing the opening angles of the cones in this way helps avoid the scattering/diffraction pattern arriving at the detector that is arranged for detecting the absorption data; and vice versa.

The method described above is an angular dispersive technique, although it can also be embodied as an energy dispersive technique.

Visualisation technique of playing as a movie could be applied both to the absorption and to the scattering data, and to the combined data. Data can be extracted from the absorption data by applying a matching algorithm to track features throughout the sequence. They are treated as a stereo pair, a set of multiple view images. A plurality of sensors around the ring—each produces a full scan because they are translated in x and y directions. For example, if we consider sensors at opposite sides of the ring, a binocular stereo pair image could be formed. matching algorithms could be applied to identify corresponding features in the pairs. There is parallax in the radial direction. This is possible because in a direct tomography method we know where the voxel is because of the imaging geometry.

The above diagrams show operation in a transmissive mode. It is to be appreciated that in alternative embodiments reflective mode imaging could be employed.

It will be appreciated that the display of the captured images is not essential. For example, a machine could be set up to emit an audio or visual alarm when a particular material is identified. That identification can be achieved automatically rather than as part of an image display process.

The disclosure combines high spatial resolution X-ray absorption data (or imagery) with coherently scattered or diffracted X-rays to provide unique XRD signatures for crystalline materials such as: manufactured materials such as metals, alloys, ceramics, cements; minerals such as rocks, salts, soils; Organic materials such as drugs, chemicals, sugars, proteins, etc; and has applications in security imaging, forensics—drug detection; non-destructive testing & evaluation (NDT&E); production (quality assurance, process control); instrumentation; and medical diagnostics.

Figure 10:
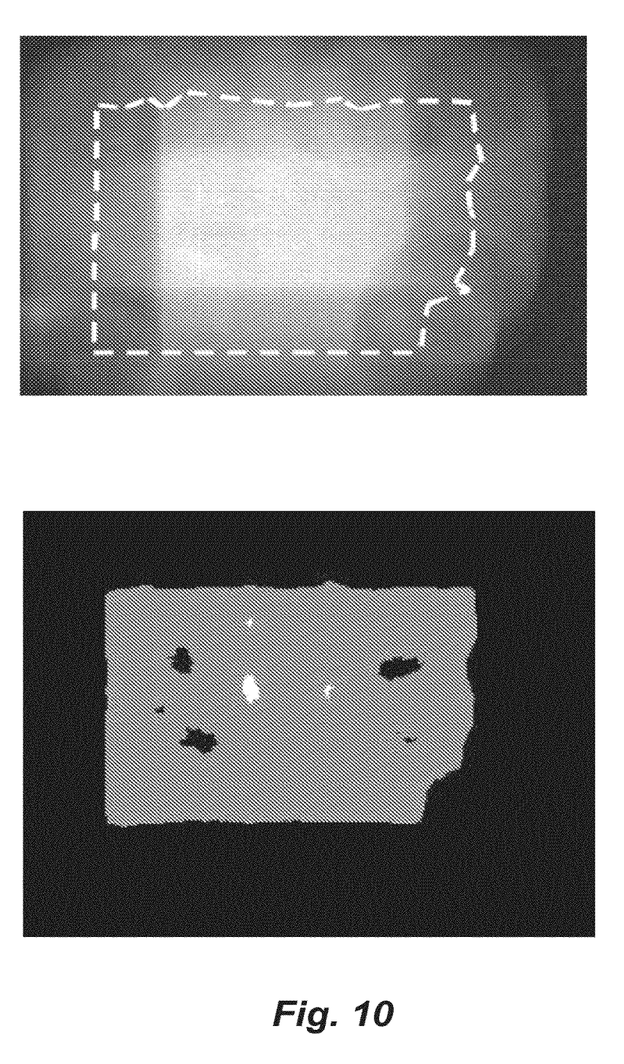
FIG. 10 shows example images that can be produced according to an embodiment.

FIG. 10 shows example images obtained according to the above. Testing and evaluation of the concept with various arrangements of objects fabricated from a range of different materials was carried out. FIG. 10.1 illustrates a simple example of a "raw diffraction" image collected over a 50 mm×35 mm Alumina sheet. The sensing arrangement focussed on depth planes normal to the symmetry axis of the interrogating X-tray beam. Quantising the 2-Theta foci produced by the Alumina provides the intensity values of the pixels that comprise the resultant diffraction image (the dashed outline represents the relative position of the sheet). The intensity radiation around the periphery of the image is due to the diameter of the tubular interrogating X-ray beam extending beyond the periphery of the sheet. Deconvolving this data with the appropriate aperture restores the outline of the image as shown in FIG. 10.2 ring sensor collects absorption data from a circular path about each diffraction focus. Synthesis of the ring data produces laminographic information. The mapping of the diffraction images to the corresponding laminograms, by virtue of a common X-ray beam geometry, provides the basis for a new 3D imaging modality.

The increased intensity of the diffraction signals has important implications for applications which demand high speed acquisition of diffraction data.

The invention has utility for distinguishing between materials, as mentioned above. This includes materials that exhibit little or no long range order, such as liquids or even gases.

The invention can be implemented as a machine or as part of a machine, for example as part of an airport security scanner, an inspection apparatus in a factory or for any of the purposes outlined above. Aspects of the invention may also be embodied as control software for controlling the operation of such machines. The machine may comprise a computer. The computer can be loaded or provided with software which it can execute to perform the analysis and display of the image data and/or for controlling the operation of the machine. The computer may be formed by taking a general purpose computer, and storing software on the computer, for example making use of a computer readable medium as mentioned above. When that general purpose computer executes the software, the software causes it to operate as a new machine. The invention is also a process (or alternatively, a "method"—the steps of which are set out herein), and the images that are produced are considered as products obtained directly by means of the process.

Various improvements and modifications can be made to the above without departing from the scope of the invention. The techniques can be employed in a reflection mode, effectively functioning as a surface inspection technique, which may be useful for analysis of sheets in industrial and other applications.

The invention claimed is:

1. A method of sample analysis comprising:
   irradiating a sample with electromagnetic radiation which comprises at least one tubular beam;
   collecting electromagnetic radiation absorption data from a plurality of translationally scanned object positions;
   collecting electromagnetic radiation scattering data;
   combining said absorption and scattering data;
   wherein said combining comprises:
   obtaining position information from the absorption data;
   matching a feature in the absorption data with a feature in the scattering data; and
   corresponding the position information from the absorption data to the scattering data.

2. The method of claim 1, wherein a shape of the tubular beam is a right circular cylinder or a cone.

3. The method of claim 1, wherein the tubular beam is formed by passing the electromagnetic radiation rays through a collimator that comprises an electromagnetic radiation blocking body portion and one or more electromagnetic radiation transmitting apertures, a shape of which defines a shape of the tubular beam or beams.

4. The method of claim 1, wherein the collection of electromagnetic radiation absorption data comprises a laminographic technique.

5. The method of claim 1, wherein the collection of electromagnetic radiation scattering data comprises placing a detector in a plane where Debye cones diffracted from the sample overlap at a central point.

6. The method of claim 1, comprising irradiating electromagnetic radiation in a first conical beam having a first opening angle, and a second conical beam having a second opening angle.

7. The method of claim 6, wherein both conical beams share a common point source.

8. The method of claim 6, wherein the relative opening angles of the first and second conical beams are chosen such that both beams are directed towards different detectors or different portions of a detector so that the interference of signals detected by one detector or one detector portion and signals detected by the other detector or other detector portion is reduced or minimised.

9. The method of claim 1, wherein a sequence of images is displayed to a user.

10. The method of claim 1, wherein the electromagnetic radiation comprises X-rays.

11. A method of material identification and/or discrimination comprising:
performing a method of sample analysis according to claim 1; and
matching the combined absorption and scattering data with known material characteristics.

12. A sample analysis apparatus, comprising:
an electromagnetic radiation source arranged to irradiate at least one tubular beam;
a detector for collecting electromagnetic radiation absorption data from a plurality of translationally scanned object positions;
a detector for collecting electromagnetic radiation scattering data;
a processor for combining said absorption and scattering data;
wherein said processor is configured to:
obtain position information from the absorption data;
match a feature in the absorption data with a feature in the scattering data; and
correspond the position information from the absorption data to the scattering data.

13. The apparatus of claim 12, wherein the detector for collecting electromagnetic radiation absorption data and the detector for collecting electromagnetic radiation scattering data are provided as different portions of a master detector.

14. The apparatus of claim 12, wherein the detector for collecting electromagnetic radiation absorption data comprises a ring sensor.

15. The apparatus of claim 14, wherein the detector for collecting electromagnetic radiation scattering data is provided within the bounds of the ring sensor.

16. A computer-program product comprising a computer-usable medium having computer-readable program code embodied therein, the computer-readable program code adapted to be executed to implement the method of claim 1.

* * * * *